United States Patent
Bremer et al.

(10) Patent No.: US 7,530,258 B2
(45) Date of Patent: May 12, 2009

(54) METHOD FOR THE PREPARATION OF SAMPLES FOR AN ANALYZER AND SAMPLE PREPARATION STATION THEREFOR

(75) Inventors: Dirk Bremer, Duisburg (DE); Bernhard Rose, Düsseldorf (DE)

(73) Assignee: Gerstel Systemtechnik GmbH & Co. KG (DE)

( * ) Notice: Subject to any disclaimer, the term of this patent is extended or adjusted under 35 U.S.C. 154(b) by 148 days.

(21) Appl. No.: 11/608,684

(22) Filed: Dec. 8, 2006

(65) Prior Publication Data

US 2007/0140904 A1    Jun. 21, 2007

(30) Foreign Application Priority Data

Dec. 16, 2005    (DE) .................. 10 2005 060 303

(51) Int. Cl.
*G01N 33/48* (2006.01)

(52) U.S. Cl. .................. 73/23.41; 73/863.21; 422/68.1; 422/89

(58) Field of Classification Search ............... 73/23.41, 73/863.21; 422/68.1, 89
See application file for complete search history.

(56) References Cited

U.S. PATENT DOCUMENTS

| | | | | |
|---|---|---|---|---|
| 5,686,656 A | * | 11/1997 | Amirav et al. ............. | 73/23.41 |
| 2005/0014156 A1 | * | 1/2005 | Pawliszyn ..................... | 435/6 |

FOREIGN PATENT DOCUMENTS

| | | |
|---|---|---|
| DE | 69504635 T2 | 5/1999 |
| DE | 10219790 C1 | 10/2003 |
| DE | 60011685 D | 7/2004 |
| DE | 11200500310 T | 3/2007 |

* cited by examiner

*Primary Examiner*—Daniel S Larkin
(74) *Attorney, Agent, or Firm*—Townsend and Townsend and Crew LLP; Kenneth R. Allen

(57) ABSTRACT

A method is provided for the preparation of samples for an analyzer, and a sample preparation station therefor, which allows injection of even relatively large liquid volumes through a packing in an automated manner in order to enrich the packing of the substances of a sample which are to be investigated.

23 Claims, 3 Drawing Sheets

METHOD FOR THE PREPARATION OF SAMPLES FOR AN ANALYZER AND SAMPLE PREPARATION STATION THEREFOR

CROSS-REFERENCES TO RELATED APPLICATIONS

See Application Data Sheet

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The invention relates to a method for the preparation of samples for an analyzer and to a sample preparation station therefor.

For the adsorption and/or sorption of analytes, it is known to use cartridges with packings located therein, through which respective sample material is induced to flow, in order to analyze the analytes qualitatively and/or quantitatively later by means of a respective analyzer, for example by means of a liquid or gas chromatograph. However, this requires complicated manual handling.

DE 102 19 790 C1 discloses a handling device for samples for an analyzer, the handling device comprising a gripper which is movable along three axes perpendicular to one another and by means of which different samplers, such as, for example, different syringes and also sample tubes equipped with transporting heads, can be handled.

BRIEF SUMMARY OF THE INVENTION

According to the invention, a method is provided for the preparation of samples for an analyzer, and a sample preparation station therefor, which allows injection of even relatively large liquid volumes through a packing in an automated manner in order to enrich the packing of the substances of a sample which are to be investigated.

A specific embodiment of the invention is a method for the preparation of samples for an analyzer, in particular a chromatograph, wherein a sample discharger is used which is movable between a sample discharge position and an elution position and which comprises a holder for a receptacle, movable and detainable therein, for a cartridge, provided with a packing for the reception of analytes, with a syringe needle, with a sealing and with a transporting head, further wherein a cartridge is inserted into the receptacle of the sample discharger located in the sample discharge position, sample material is injected at least once by means of an injector through the sealing into the cartridge and, after flowing through the packing, is discharged through the first syringe needle, an empty sample container is arranged in the elution position, the sample discharger, together with the laden cartridge, are moved into the elution position, and the receptacle, together with the cartridge, are detained in the holder of the sample discharger, and at least one eluent is injected at least once by means of an injector through the sealing into the cartridge and is discharged through the syringe needle into the sample container, the cartridge, sample container and injector being handled automatically.

According to a further embodiment of the invention, a sample preparation station for samples for an analyzer, in particular a chromatograph, comprises a sample discharger which is movable between a sample discharge position and an elution position and which comprises a holder for a receptacle, movable and detainable therein, for a cartridge, provided on the outlet side with a first syringe needle, on the inlet side with a sealing and a transporting head and with a packing for the reception of analytes, at least one injector and at least one automatic handling device, by means of which cartridges, the at least one injector and the sample container can be handled.

It thereby becomes possible to use commercially available cartridges with packings or for self-packing as once-only articles, on which analytes can be enriched even out of relatively large liquid volumes in an automated manner.

Further embodiments of the invention may be gathered from the following description and the claims.

The invention is explained in more detail below with reference to exemplary embodiments illustrated in the accompanying figures.

DETAILED DESCRIPTION OF THE INVENTION

Figure 1:
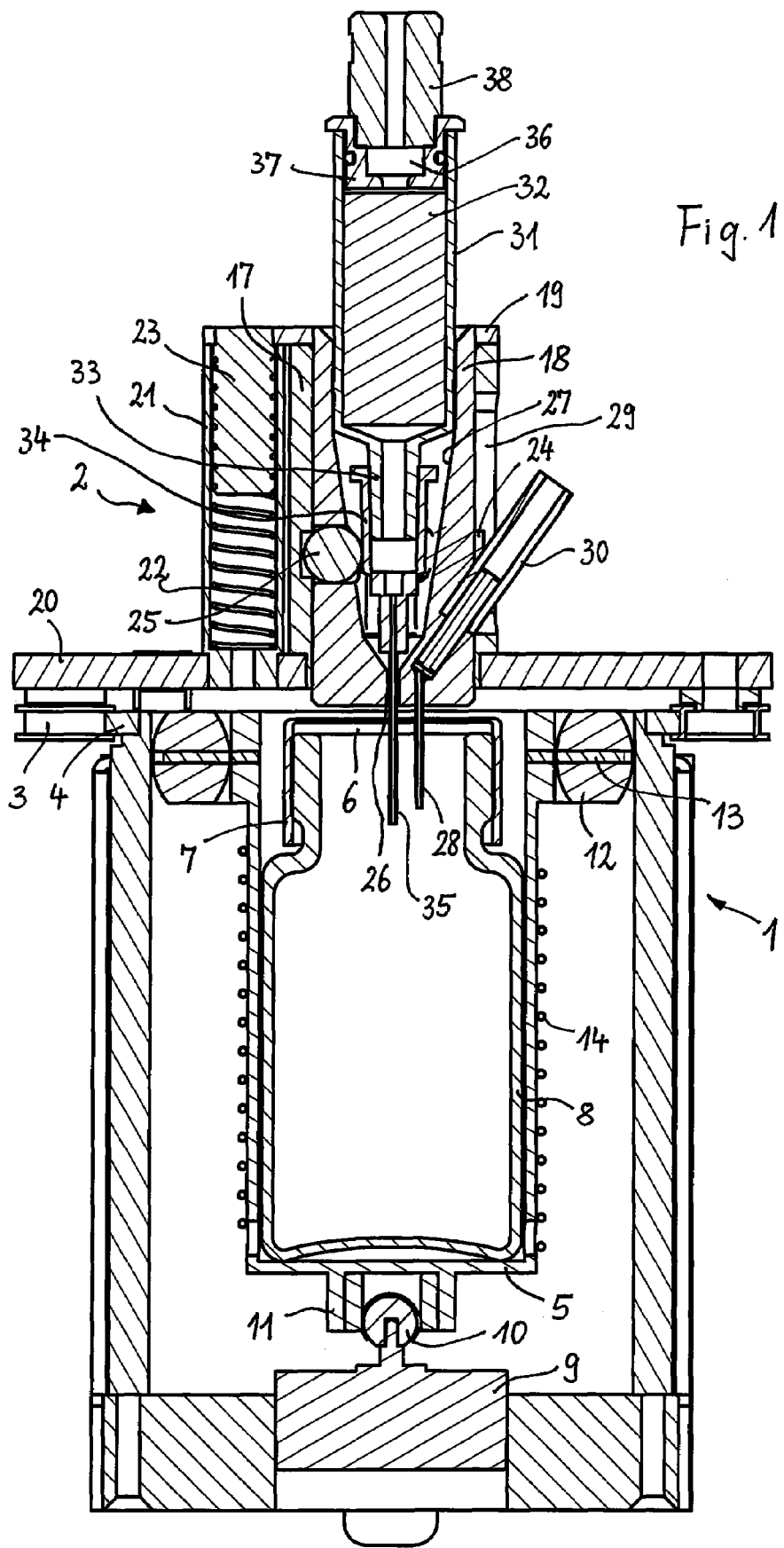
FIG. 1 shows an embodiment of a sampling station in cross-sectional view in the form of a detail.
Figure 2:
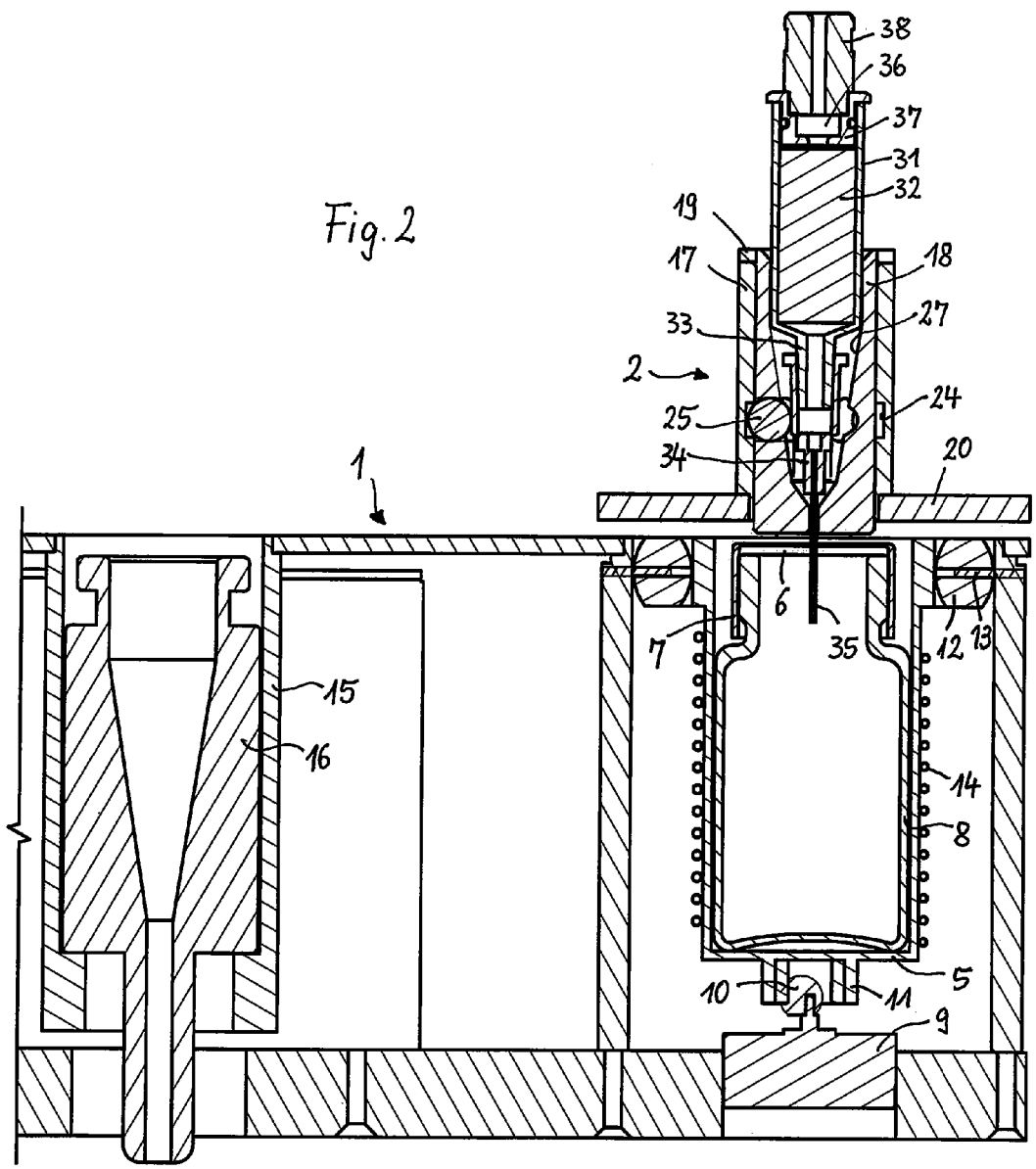
FIG. 2 shows in the form of a detail a cross-sectional view, rotated at 90°, through the sampling station of FIG. 1.
Figure 3:
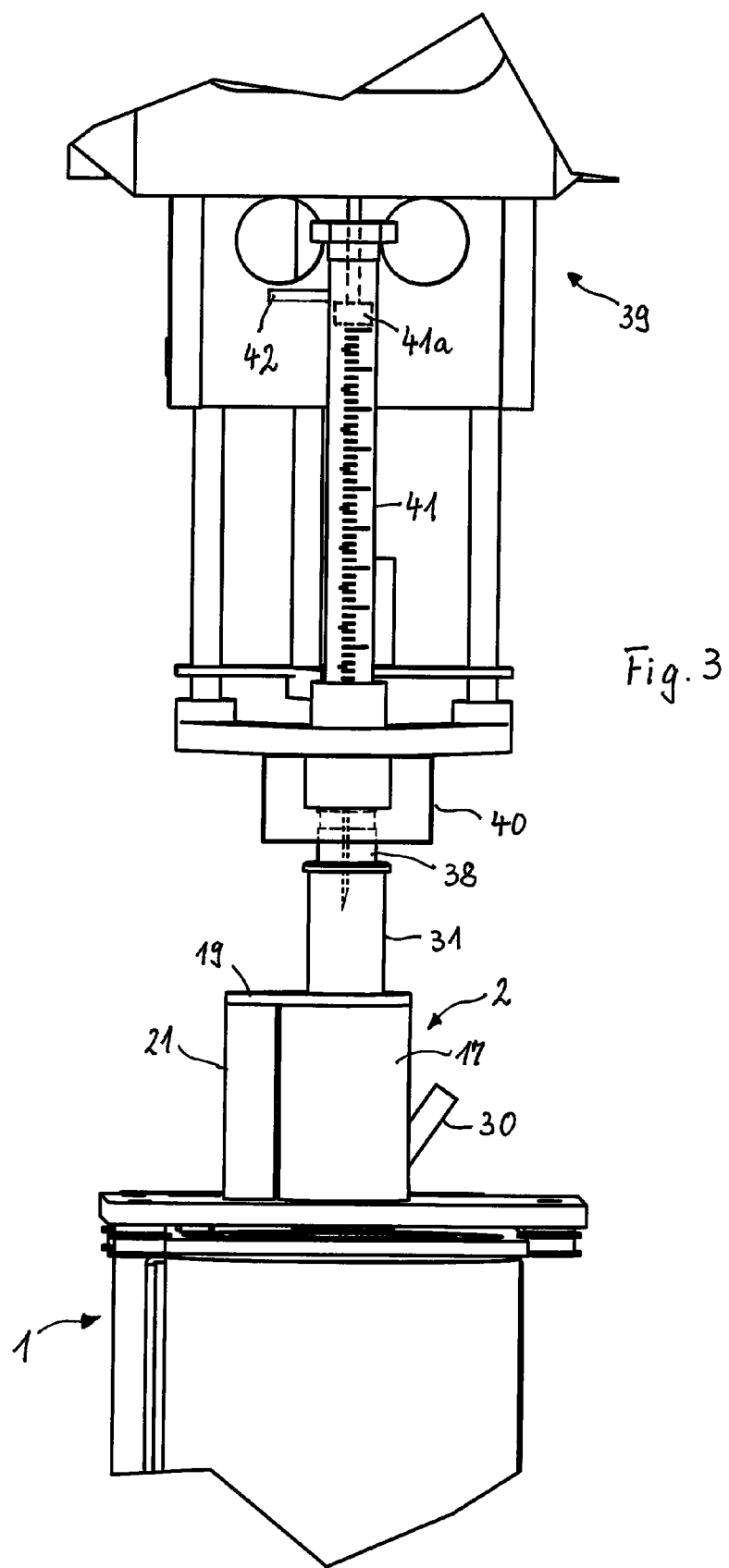
FIG. 3 shows in the form of a detail the sampling station of FIG. 1 during a conditioning operation.

The sampling station illustrated in FIGS. 1 and 2 comprises a mount or stand 1 with a slide shaped sample discharger 2 which is movable (or pivotable, not illustrated) via rollers 3 along rails 4 between two positions. One of these positions is used as the sample discharge position and the other as the elution position. Located in the elution position is a trough like container holder 5 for receiving a sample container 8, in this exemplary embodiment a vial, provided with a cap 7 holding a septum 6.

Expediently, it is provided that the sample collected in the respective sample container 8, which is in the elution position, can be shaken. For this purpose, it may be provided that the sample container 8 contains a magnetic stirring element, whilst a device generating an alternating magnetic field is arranged below the container holder 5 in order to generate a stirring movement of the stirring element. Stirring or agitation may also be carried out by means of ultrasound.

Furthermore, a shaking of the container holder 5 and consequently of the sample in the sample container 8 received by the container holder 5 may be provided. For this purpose, expediently, the container holder 5 is suspended cardanically at its upper end and can be driven via an electric motor 9. During operation, the electric motor 9 drives a ball 10, arranged eccentrically on the shaft of the electric motor 9, at a controlled speed, the ball 10 being arranged in a central hollow journal 11 below the bottom of the container holder 5 and, via its eccentric arrangement, subjecting the container holder 5, on account of the cardanic suspension at its upper end, and, consequently, a sample container 8 located therein to a rotating, pivoting movement.

The cardanic suspension may take place via a cambered ring 12 which is mounted on the stand 1 via two axes 13 arranged opposite one another at 180° and on which the container holder 5 is mounted via two further axes 13 offset at 90° thereto.

For the evaporation and, if appropriate, derivatization of sample material in the sample container 8, it is expedient to surround the container holder 5 with a heating device, for example, in the form of a heating coil 14.

Located in the sample discharge position is a holder 15 with a discharge funnel 16, to the lower end of which a discharge line can be connected. If appropriate, the discharge funnel 16 may be provided on the inlet side with a septum.

The sample discharger 2 comprises a sleeve-shaped holder 17 for a receptacle 18. The receptacle 18 is connected on the top side to a plate 19, whilst, on a bottom plate 20 of the sample discharger 2, a plurality of cylinders 21 are arranged, which receive springs 22 which are supported on the bottom side and on the top side are supported on the plate 19 or guide inserts 23 carried by the latter and correspondingly prestress the receptacle 18 in the direction away from the bottom plate 20. The holder 17 comprises on the inside a peripheral groove 24, whilst the receptacle 18 receives captively balls 25 which can be pressed into the groove 24 in order to detain the receptacle 18 in the holder 17. Furthermore, the receptacle 18 comprises an inner space 27 narrowing as far as a bottom-side passage orifice 26 and carries a syringe needle 28 which projects on the bottom side and which is connected to a connection part 30 projecting outwards through a vertical slot 29 of the holder 17. The upper end of the slot 29 in this case serves at the same time as a stop for the non-detained receptacle 18 pressed upwards by the springs 22.

The receptacle 18 serves for receiving a cartridge 31 in the form of a syringe body and consisting, for example, of glass or plastic, which inside it receives a packing 32 of adsorbing and/or sorbing material and on its extension 33 receives an attachment 34 with a syringe needle 35. At the end lying opposite the syringe needle 35, the cartridge 31 is closed by means of an insert 37 which abuts sealingly against the inner wall of the cartridge and has a central orifice covered by a sealing 36 and which carries a transporting head 38 extending outwards. The sealing 36 may be a membrane or a cartridge septum.

The cartridge 31 can be inserted into the receptacle 18, the attachment 34 pressing outwards the balls 25 which, with the receptacle 18 pressed correspondingly far into the holder 17, latch into the groove 24. By the cartridge 31 being pulled up via the transporting head 38, the balls 25 can be pressed out of the groove 24 again by the springs 22 and the receptacle 18 pressed upwards until the connection part 30 comes to an abutment in the slot 29.

A freely programmable automatic handling device 39, which may comprise a gripper 40 which is movable in three axes perpendicular to one another and by means of which the cartridge 31 provided with a transporting head 38 can be handled, is described in DE 102 19 790 C1. Sample containers 8 with a magnetizable cap 7 can thereby also be handled if the gripper 40 of the handling device 39 is designed for holding the sample container 8 or is provided for this purpose, for example, with inserted permanent magnets which can hold the sample container 8 via its magnetizable cap 7. If appropriate, a further gripper, exchangeable for the gripper 40, for example by rotation, or a second handling device may also be used for the sample container 8.

The procedure is then as follows:

First, cartridges 31 are prepared thus far as disposable material and are stored in a magazine. This is performed expediently such that their syringe needles 35 are pierced through sealings, particularly septa, located in the magazine, so that the cartridges 31 are received, in a sealed manner. If appropriate, the dead space above the packing 32 of the cartridges 31 is reduced.

By means of the handling device 39, a cartridge 31 removed from the magazine is inserted into the receptacle 18 of the sample discharger 2 which is in the sample discharge position, with the receptacle 18 being detained.

Thereafter, expediently, a conditioning of the cartridge 31 or of the packing 32 is performed first by injecting solvent through the sealing 36 into the cartridge 31 and emptying it through the syringe needle 35 into the discharge funnel 16 by means of an injector 41 which is an injection syringe or an injection needle connected to a pump, for example a hose pump or the like. If appropriate, this may be continued with further solvents which are taken, for example, through the injector 41 out of a respective bottle battery.

Subsequently, the sample discharge is performed by taking out sample material from a respective container, for example a vial, or a throughflow cell by means of the same or a further injector 41 and injecting it into the cartridge 31 through the sealing 36. In order to allow a respective quantity of sample material flowing through the packing 32 even when an injection syringe is used as the injector 41, this may even be carried out several times. Analytes adsorbed and/or sorbed by the packing 32 remain on the latter, whilst the rest passes through the injection needle 35 into the discharge funnel 16.

The packing 32 may, if appropriate, be dried before and/or after the sample discharge, by, if appropriate, leading through heated inert gas. This may be performed via the injection needle of the injector 41. For example, if an injection syringe is used as the injector 41, this may have a lateral gas connection 42, above which the piston 41a of the injection syringe must be drawn back for the ingress of gas. This may be carried out automatically, in a respectively programmed manner, by means of the handling device 39.

A sample container 8 is arranged in the elution position by means of the handling device 39.

When the sample discharge in the sample discharge position is terminated and the sample container 8 is in the elution position, the cartridge 31 is drawn up by means of the handling device 39 to an extent such that the receptacle 18 is released from its detention with the holder 17, so that the syringe needles 28, 35 are drawn back and therefore the sample discharger 2 can be moved into the elution position.

After the sample discharger 2 has assumed its position above the sample container 8 in the elution position, the cartridge 31, together with the packing 32 laden with analytes, is pressed into the receptacle 18 by means of the handling device 39, and consequently the latter into its holder 17, and detained. The syringe needles 28, 35 thereby penetrate the septum 6 of the sample container 8.

By means of the injector 41, eluent is injected through the sealing 36 into the cartridge 31, if appropriate several times and if appropriate also in the form of different solvents, with the result that the eluent flows through the packing 32 and, laden with analytes, passes through the syringe needle 35 into the sample container 8. The gas volume contained in the latter can escape through the second syringe needle 28 and the connection part 30.

If appropriate, again, a drying operation may follow, in which, for example with the cartridge 31 drawn out, inert gas is introduced into the sample container 8 via the injection needle of the injector 41 and is discharged again via the syringe needle 28 pressed into the sample container 8 by means of the injector 41 via the receptacle 18. In this case, for the purpose of assisting the evaporation of the solvent, the sample container 8 may be heated by means of the heating device 14. During the drying operation, deaeration may be performed via the connection part 30, if appropriate with the assistance of a vacuum.

It may then be necessary to treat the analytes which have remained in the sample container 8 once again with a solvent which is supplied via the injector 41. For this purpose, the sample container 8 can be shaken by means of the electric motor 9 or the material in the sample container 8 can be agitated magnetically or by means of ultrasound. A derivatization step may also follow.

Subsequently, the sample container 8 can be arranged in a magazine, in order to take out sample material later for a, in particular, chromatographic analysis, or, by means of a removal syringe handled by the handling device 39, sample material can be directly taken out through the septum 6 and supplied to an analyzer.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for preparation of samples for an analyzer wherein
    a sample discharger is used which is movable between a sample discharge position and an elution position and which comprises a holder for a receptacle, movable and detainable therein, for a cartridge, provided with a packing for the reception of analytes, with a first syringe needle, with a sealing and with a transporting head;
    the cartridge is inserted into the receptacle of the sample discharger located in the sample discharge position;
    sample material is injected at least once by means of an injector through the sealing into the cartridge and, after flowing through the packing, being discharged through the first syringe needle;
    an empty sample container is arranged in the elution position;
    the sample discharger, together with the cartridge, is moved into the elution position, and the receptacle, together with the cartridge, being detained in the holder of the sample discharger; and
    at least one eluent is injected at least once by means of the injector through the sealing into the cartridge and being discharged through the first syringe needle into the sample container,
    the cartridge, sample container and injector being handled automatically.

2. The method according to claim 1, wherein the receptacle, which carries a further syringe needle connected to an external connection part, and a sample container provided with a container septum are used, the container septum being pierced by the two syringe needles during the movement of the sample discharger, together with the cartridge, into the elution position.

3. The method according to claim 1, wherein the packing of the cartridge is conditioned, before the injection of the sample material, by the injection of at least one solvent.

4. The method according to claim 1, wherein the sample material is taken out from a sample container via the injector.

5. The method according to claim 1, wherein the sample material is taken out from a throughflow cell by means of the injector.

6. The method according to claim 1, wherein a syringe or an injection needle supplied by a pump is used as the injector.

7. The method according to claim 1, wherein the packing of the cartridge is dried after the sample discharge.

8. The method according to claim 1, wherein the eluted sample received by the sample container is dried.

9. The method according to claim 8, wherein the dried sample is treated again with solvent injected by means of the injector.

10. The method according to claim 9, wherein the sample and the solvent are moved mixingly for treatment.

11. The method according to claim 10, wherein the sample container is shaken.

12. A sample preparation station for samples for an analyzer comprising:
    a sample discharger which is movable between a sample discharge position and an elution position and which comprises a holder for a receptacle, movable and detainable therein, for a cartridge, provided on an outlet side with a first syringe needle, on an inlet side with a sealing and a transporting head and with a packing for the reception of analytes;
    at least one injector, and
    at least one automatic handling device, by means of which the cartridge, the at least one injector and the sample discharger can be handled.

13. The sample preparation station according to claim 12, wherein the receptacle carries a further syringe needle connected to an external connection part.

14. The sample preparation station according to claim 12, wherein the sample discharger is movable in a slide-like manner between the sample discharge position and the elution position.

15. The sample preparation station according to claim 12, wherein the receptacle can be pressed into its holder and detained counter to a spring force.

16. The sample preparation station according to claim 15, wherein the receptacle can be pressed into its holder and detained by means of the cartridge.

17. The sample preparation station according to claim 12, wherein the receptacle carries at least one ball which, as a result of the introduction of a cartridge, can be pressed into a groove in the holder.

18. The sample preparation station according to claim 12, wherein a discharge funnel is arranged in the sample discharge position.

19. The sample preparation station according to claim 12, wherein a container holder for a sample container is arranged in the elution position.

20. The sample preparation station according to claim 19, wherein the container holder is heatable.

21. The sample preparation station according to claim 12, wherein the sample contained in a sample container received by the container holder is intermiscible.

22. The sample preparation station according to claim 21, wherein the container holder is shakeable.

23. The sample preparation station according to claim 22, wherein the container holder is suspended cardanically at its upper end and on its underside has an eccentric drive.

* * * * *